(12) United States Patent
Isserow et al.

(10) Patent No.: US 10,010,445 B2
(45) Date of Patent: Jul. 3, 2018

(54) TREATMENT DEVICE USING NANOTECHNOLOGY

(71) Applicants: Jonathan Isserow, Basking Ridge, NJ (US); Laura Isserow, Basking Ridge, NJ (US)

(72) Inventors: Jonathan Isserow, Basking Ridge, NJ (US); Laura Isserow, Basking Ridge, NJ (US)

(73) Assignees: Jonathan Isserow, Basking Ridge, NJ (US); Laura Isserow, Basking Ridge, NJ (US)

( * ) Notice: Subject to any disclaimer, the term of this patent is extended or adjusted under 35 U.S.C. 154(b) by 457 days.

(21) Appl. No.: 13/747,584

(22) Filed: Jan. 23, 2013

(65) Prior Publication Data

US 2014/0207216 A1    Jul. 24, 2014

(51) Int. Cl.
*A61F 7/08*    (2006.01)
*A61F 7/00*    (2006.01)
*A61F 7/02*    (2006.01)

(52) U.S. Cl.
CPC ...... *A61F 7/007* (2013.01); *A61F 2007/0071* (2013.01); *A61F 2007/0078* (2013.01);
(Continued)

(58) Field of Classification Search
CPC ............. A61L 2400/04; A61L 2400/12; Y10S 977/931; Y10S 977/961
(Continued)

(56) References Cited

U.S. PATENT DOCUMENTS

| 5,658,583 A | 8/1997 | Zhang et al. |
| 6,205,016 B1 | 3/2001 | Niu |

(Continued)

FOREIGN PATENT DOCUMENTS

| WO | 2010123528 | 10/2010 |
| WO | WO 2010123528 A2 | 10/2010 |

(Continued)

OTHER PUBLICATIONS

Trevor J. Simmons et. al., Applications of Carbon Nanotubes to Wound Healing Biotechnology, Dec. 7, 2012, Nanomaterials for Biomedicine, vol. 1119, pp. 155-174.*

(Continued)

*Primary Examiner* — Linda Dvorak
*Assistant Examiner* — Yasamin Ekrami
(74) *Attorney, Agent, or Firm* — Gearhart Law LLC

(57) ABSTRACT

The current invention discloses a treatment device having a heat source, a power source and a heat applicator. The power source includes at least one nanotech battery, ensuring superior properties such as prolonged electricity production and prompt recharging. The heat applicator includes a heat conductive layer made from nanofibers, providing highly efficient heat distribution to the targeted regions. The power source provides energy to the heat source, which generates heat so that the applicator may distribute to an injury site or wound bed of a user. The current device may also be used for cooling, instead of heating applications. In addition to the medical utilizations, the current device may also play a central role in other apparatus that require thermal control capabilities.

5 Claims, 1 Drawing Sheet

(52) U.S. Cl.
CPC ............... *A61F 2007/0093* (2013.01); *A61F 2007/0226* (2013.01); *A61F 2007/0246* (2013.01); *A61F 2007/0247* (2013.01)

(58) Field of Classification Search
USPC ............................. 607/96–99, 108–112, 114
See application file for complete search history.

(56) References Cited

U.S. PATENT DOCUMENTS

| | | | |
|---|---|---|---|
| 6,283,931 B1* | 9/2001 | Augustine | A61F 7/007 602/14 |
| 6,414,836 B1 | 7/2002 | Tennent et al. | |
| 6,586,133 B1* | 7/2003 | Teeters et al. | 429/152 |
| 6,665,169 B2 | 12/2003 | Tennent et al. | |
| 7,116,546 B2 | 10/2006 | Chow et al. | |
| 7,579,077 B2 | 8/2009 | Dubrow et al. | |
| 7,789,930 B2 | 9/2010 | Ensor et al. | |
| 7,813,807 B2* | 10/2010 | Franklin | A61N 1/0551 607/3 |
| 7,972,616 B2 | 7/2011 | Dubrow et al. | |
| 8,025,960 B2 | 9/2011 | Dubrow et al. | |
| 8,057,841 B2 | 11/2011 | Reneker et al. | |
| 8,133,264 B1 | 3/2012 | LaFontaine | |
| 8,269,058 B2* | 9/2012 | McCarthy et al. | 602/41 |
| 8,664,572 B2* | 3/2014 | Bridges | 219/212 |
| 2002/0026226 A1 | 2/2002 | Ein | |
| 2002/0082668 A1* | 6/2002 | Ingman | A61F 13/126 607/98 |
| 2003/0036715 A1* | 2/2003 | Knutson | A61F 15/008 602/43 |
| 2005/0228806 A1 | 2/2005 | Kumamoto et al. | |
| 2005/0261670 A1* | 11/2005 | Weber | A61L 29/126 606/21 |
| 2006/0122596 A1* | 6/2006 | Dubrow | A61F 13/00 606/60 |
| 2006/0142816 A1 | 6/2006 | Fruitman | |
| 2006/0204738 A1* | 9/2006 | Dubrow et al. | 428/292.1 |
| 2006/0282134 A1 | 12/2006 | Shapiro et al. | |
| 2007/0108190 A1* | 5/2007 | Ferguson | A61F 7/007 219/545 |
| 2008/0023394 A1 | 1/2008 | Naruse et al. | |
| 2008/0069848 A1 | 3/2008 | Peters | |
| 2008/0069905 A1 | 3/2008 | Peters | |
| 2008/0071206 A1 | 3/2008 | Peters | |
| 2008/0109941 A1 | 5/2008 | Moreshead | |
| 2008/0141681 A1* | 6/2008 | Arnold | A41D 13/005 62/3.5 |
| 2008/0294161 A1* | 11/2008 | Wolf, Jr. | A61B 18/082 606/49 |
| 2009/0163984 A1 | 6/2009 | Robinson et al. | |
| 2010/0021819 A1 | 1/2010 | Zhamu et al. | |
| 2010/0280584 A1* | 11/2010 | Johnson et al. | 607/116 |
| 2010/0285972 A1 | 11/2010 | Dubrow et al. | |
| 2010/0312313 A1* | 12/2010 | Ferguson | A61F 7/007 607/99 |
| 2011/0064785 A1 | 3/2011 | Daniels et al. | |
| 2011/0152643 A1* | 6/2011 | Xue et al. | 600/309 |
| 2011/0170236 A1 | 7/2011 | Young | |
| 2011/0201984 A1 | 8/2011 | Dubrow et al. | |
| 2011/0218601 A1 | 9/2011 | Uchiyama | |
| 2011/0309774 A1 | 12/2011 | Peng et al. | |
| 2012/0022620 A1 | 1/2012 | Khodak et al. | |
| 2012/0130459 A1* | 5/2012 | Kim et al. | 607/115 |
| 2012/0157904 A1* | 6/2012 | Stein | 602/43 |
| 2012/0172953 A1* | 7/2012 | Chen | A61F 7/007 607/98 |
| 2012/0256704 A1* | 10/2012 | Johnson et al. | 333/185 |
| 2013/0096518 A1* | 4/2013 | Hall et al. | 604/319 |
| 2013/0176699 A1* | 7/2013 | Tonchev et al. | 361/760 |
| 2013/0274896 A1* | 10/2013 | Wang | A61F 2/7812 623/36 |
| 2014/0318699 A1* | 10/2014 | Longinotti-Buitoni et al. | 156/247 |

FOREIGN PATENT DOCUMENTS

| | | |
|---|---|---|
| WO | WO 2010123528 A3 | 10/2010 |
| WO | 2011112364 | 9/2011 |
| WO | WO 2011112364 A1 | 9/2011 |

OTHER PUBLICATIONS https://www.nonoskin.com.

Ruetzler, Kurt, M.D., et al; Forced-Air and a Novel Patient-Warming System (vitalHEAT vH2) Comparably Maintain Normothermia During Open Abdominal Surgery; www.anesthesia-analgesia.org; Mar. 2011; vol. 112; No. 3; pp. 608-614.

Using Freezing Conditions to Kill Bed Bugs, webpage from https://web.archive.org/web/20121115095l0/http://www.bedbugs.umn.edu/bed-bug-control-in-residences/using-freezing-temperatures-for-bedbug-control, University of Minnesota (Nov. 15, 2012).

Expert Witness/Entomology, webpage from https://web.archive.org/web20120531100823/http://insectexpertphd.com/mites/aspx, (May 31, 2012).

Izri A and Chosidow O. Efficacy of Machine Laundering to Eradicate Head Lice: Recommendations to Decontaminate Washable Clothes, Linens, and Formites. Jan. 15, 2006, Clinical Infectious Diseases, 42 e:9-10.

Wainwright, Mark, Photodynamic Antimicrobial Chemotherapy (PACT), Journal of Antimicrobial Chemotherapy, 1998, pp. 13-28, vol. 42, The British Society for Antimicrobial Chemotherapy.

Suh, HJ, et al., The Combined Effect of a Three-Channel Electrode Delivery System with Local Heat on the Healing of Chronic Wounds., Diabetes Technol Ther., Oct. 2009, pp. 681-688.

Kelkarr S.S., et al., Theranostics: combining imaging and therapy., Bioconjug Chem. Oct. 19, 2011, pp. 1879-1903. Epub Aug. 29, 2011., http://www.ncbi.nlm.nih.gov/pubmed/21830812.

International Search Report for PCT Application No. PCT/US/2014/012249. dated Jun. 10, 2014. 7 pages.

* cited by examiner

TREATMENT DEVICE USING NANOTECHNOLOGY

CLAIM OF PRIORITY

This application claims no priority to any previous US patent application.

FIELD OF THE INVENTION

The current invention relates to a wound, infection, or injury treatment device and related methods. In particular, by using nanotechnology enabled heating processes, the current invention relates to a device and methods that may be used for treatment of a wound, injury, skin infection such as acne, ailment, or disease, as well as the pre-treatment to prevent wound infections prior to surgery.

BACKGROUND OF THE INVENTION

Many kinds of diseases and accidents may cause harm to the human body and results in pain, wound, infection, and injury that require both swift and continuous treatments. The treatment of such wounds/injuries has been a crucial part of healthcare. Various methods and devices have been developed to improve the quality of care that may be provided in such treatments and the healing process. Among these approaches are temperature alternation techniques, such as the application of heat or coldness by different sources.

Application of heat, or coldness, or alternating temperature changes have been widely used in the treatment of wound, infection, pain, and injury for a very long time. In addition, the heating treatment may also prevent cutaneous/skin infections as well as preventing skin infection pre-operatively. Heating treatments such as heat pads are believed to cause the dilation of blood vessels, facilitate perfusion to the target tissues and cycling of blood, and sterilize the targeting area. Cold treatments such as ice pads are believed to reduce infection and wound development, allowing quicker healing and recovery.

The temperature altering treatments, especially the application of heat, are widely in use but there are still a number of general shortcomings. For example, the heat applicators nowadays are generally bulky and difficult to fit onto small wounds or injuries at locations that are hard to access. In addition, the regular heating applicators are not long lasting, requiring frequent change of the applicator. Thirdly, some of the heat applicators are hard to reheat. In general, the existing heating application treatment devices are low in efficiency and high in waste of energy. These treatment devices cannot keep up with the development of new problem, such as the escalating crisis of multi-drug resistant infections including Methicillin-resistant *Staphylococcus aureus* (MRSA). Therefore, the development of new technology is desirable and the current invention serves as a powerful alternative to the previous devices.

Nanotechnology stands at the vanguard of integrating science and engineering and it has undergone significant progress in recent years. By using materials having nanometer level dimensions and special physical characteristics, nanotechnology has been proved to be a promising field of innovation. In particular, a number of improvements in nanotechnology using nanofibers, nanotubes, and nano-particles have enabled the production of batteries that provide higher energy density, last longer, and/or recharges faster. In addition, nanofibers have been shown to be applicable in a number of disciplines such as material science, molecular biology, and medical sciences. Nevertheless, the use of nanofibers and nanotechnology batteries in medical devices, particular treatment devices, has been scanty and leaves much to be desired. The current invention addresses such needs.

Reviewing of Related Technology:

US20080023394 discloses a medical filter material comprising a dispersion of nanofibers of thermoplastic polymer having a number average diameter of 1 to 500 nm wherein the ratio of single fibers with a diameter of more than 500 nm and 1 nm or less is 3% or less in terms of weight ratio. Further, there are provided, utilizing the medical filter material, an extracorporeal circulation column and a blood filter. Through the employment of nanofibers small in fiber diameter dispersion, high in strength and high in productivity, there can be provided a medical filter material excellent in hemadsorption performance and protein adsorption performance. Through packing with this medical filter material, there can be provided high-performance extracorporeal circulation column and blood filter.

US20080069905 teaches a therapeutic treatment device comprising a compound comprising a drug and a nitric oxide (NO) eluting polymer arranged to contact a treatment site in or on a body. The device is acting as a booster for drug eluting patches, e.g. pharmaceuticals, vitamins, nicotin, nitroglycerin, whereby with advantage two therapeutic treatments, of significant value, are combined in one treatment. A synergetic effect is achieved by such devices because NO that is eluted from the device boosts the effect of the drug, as the treatment site is more susceptible to said drug by the effect of the eluted NO.

Various devices are known in the art. Nevertheless, their structures are distinctively different from the current invention. Moreover, the other inventions fail to address all of the problems solved by the invention described herein. One embodiment of this invention is illustrated in the accompanying drawings and will be described in more detail herein below.

SUMMARY OF THE INVENTION

The current invention discloses a treatment device, and in particular a wound/infection/injury treatment device, comprising: a heat source; a heat applicator connected to the heat source; the heat applicator comprising: a heat application layer having an application surface and a heat receiving surface, and a heat conductive layer having a front side and a back side, wherein the heat conductive layer is made of nanofibers extensively affixed to the heating receiving surface of the heat application layer; and a power source connected to the heat source, empowering the heat source, the power source comprising at least one nanotech battery. Preferably, the power source and the heat source are integrated into a heat generating body directly attached to the back side of the heat conductive layer of the heat applicator, wherein the heat applicator is a layered flat structure, incorporating the heat application layer and the heat conductive layer.

Preferably, the heat conductive layer comprises nanofibers woven or unwoven but pressed into a layer that efficiently and extensively transfers heat to the heat application layer. Many specific nanofibers, nanofilaments or nanotubules may be used in the heat conductive layer. For clarity purposes, the term nanofiber is used to generally cover all the nanofibers, nanofilaments, nanotubules, and other fibrous materials having diameters between 0.5 nm and 1 um.

The power source is preferably a nanotechnology battery that possesses certain superior properties compared with conventional lithium batteries. The power source may produce higher energy density. The power source may last longer than conventional batteries. The power may also be charged and recharged promptly. In particular, nanotechnology has been used to produce "supercapacitors" that may be incorporated in rechargeable batteries. Preferably, the current treatment device employs such a supercapacitor battery allowing quick recharges.

Using the device described above, the user of the device may cause thermal alternations to the injury site or wound bed, allowing faster and more complete recovery. In particular, the device may be used to apply heat to the injury site or wound bed. The device may also be used to treat infections such as bacteria infections that are susceptible to increased temperature. The specific applications of the device are extensive.

The treatment device may further comprise a control mechanism connected to the power source. The control mechanism may be used to initiate, adjust, and end the application of thermal alternation (heat or coldness). With the control mechanism, the user of the treatment device may easily control the treatment process and change the durations, cycles, and intensity of the treatments.

In general, the present invention succeeds in conferring the following, and others not mentioned, desirable and useful benefits and objectives.

It is an object of the present invention to provide a treatment device that may be used to facilitate the healing of injuries, infections, acne, or wounds on humans and other subjects.

It is an object of the present invention to provide a treatment device that may cover the wound bed or injury site.

It is an object of the present invention to provide a treatment device that alters the temperature of a wound, infection or injury site.

It is an object of the present invention to provide a treatment device that applies heat to a wound or injury site.

It is an object of the present invention to provide a treatment device that is light and portable.

It is another object of the current invention to provide a treatment device that may be used for different kinds of wounds/infections/injuries.

It is another object of the current invention to provide a treatment device that may be used for wounds/injuries on different parts of a body, including musculoskeletal pain.

It is still another object of the current invention to provide a treatment device that is easily adjustable.

It is another object of the current invention to provide a treatment device that uses a supercapacitor battery that is easily rechargeable.

It is yet another object of the current invention to provide a treatment device that uses nanofibers for efficient heat conduction.

It is another object of the current invention to provide a treatment device that has an integrated body.

It is yet another object of the current invention to provide a treatment device that is easy to use and easy to manufacture.

DESCRIPTION OF THE PREFERRED EMBODIMENTS

Figure 1:
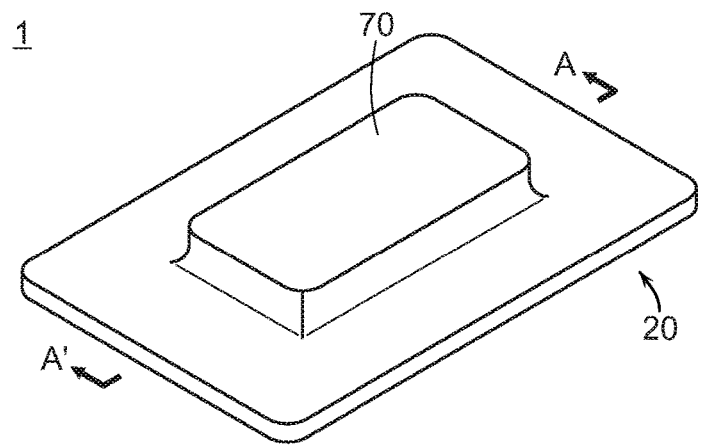
FIG. 1 shows a back perspective view of a treatment device embodying the current invention.

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

FIG. 1 shows a back perspective view of a treatment device embodying the current invention. Shown in FIG. 1 is the treatment device 1 having a heat generating body 70 attached to a heat applicator 20.

Figure 2:
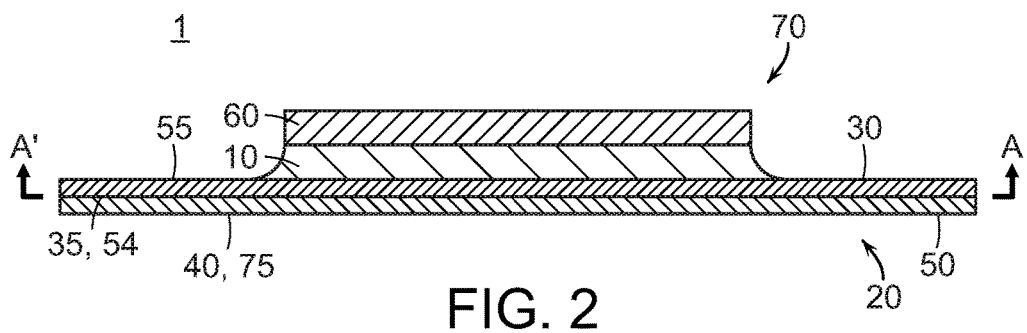
FIG. 2 shows a sectional view of the treatment device shown in FIG. 1.

FIG. 2 shows a sectional view of the treatment device shown in FIG. 1, as indicated by markers A and A'. Shown in FIG. 2 is the treatment device 1 having a heat generating body 70 attached to a heat applicator 20. The heat generating body 70 comprises a heat source 10 and a power source 60, wherein the heat source 10 and power source 60 are preferably connected by wires (not shown). In addition, the heat applicator 20 comprises a heat application layer 50 and a heat conductive layer 30, wherein the heat application layer 50 has a heat receiving surface 35 and a heat application surface 40, and the heat conductive layer 30 has a front side 54 and a back side 55. The front side 54 of the heat conductive layer 30 directly engages with the heat receiving surface 35 of the heat application layer 50. The heat application surface 40 is designed to engage exposed human wound beds or injury sites.

Figure 3:
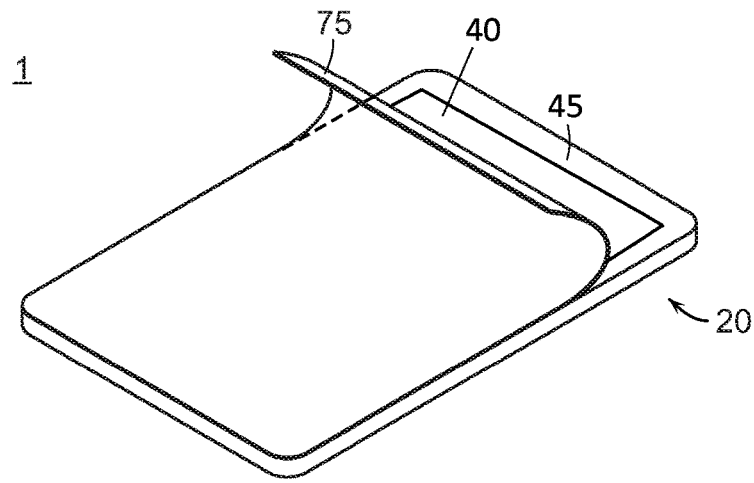
FIG. 3 shows a front perspective view of the treatment device.

FIG. 3 shows a front perspective view of the treatment device 1. Shown in FIG. 3 is the heat application surface 40 of the heat application layer 50, which is part of the heat applicator 20.

FIGS. 1, 2 and 3 show an embodiment of the current invention. However, it should be noted that the design of the current invention may vary significantly from the embodiment herein described. As long as the general inventive spirit stays consistent with the disclosure, the variations of embodiments should be considered part of the current invention. While some of the variations are hereby described, the other variations may be considered general knowledge to a person skilled in the art so that they do not required detailed discussion. The teachings and disclosures of the current invention encompass all the variations.

The power source 60 of the current invention may employ any kind of electricity generating or storing devices. Preferably, the power source here is a rechargeable battery using nanotechnology. For example, the nanotech battery may use silicon nanowires on stainless steel substrate, providing 10 times the power density of conventional lithium ion batteries. Alternatively, the nanotech battery may use aligned carbon nanotubes on a substrate to establish the anode or cathode in a conventional battery, improving the power generating capacity by almost 10 fold. More preferably, the power source is a battery utilizing nanotech supercapacitor technology, which can be recharged promptly. For instance, by using grapheme graphene on the surface of anodes to make lithium-ion batteries, the batteries may be recharged 10 times faster than common rechargeable batteries. The fast recharging nanotech batteries are particularly suitable as the power source 60 herein included in the current invention. With such designs, the treatment device may be used more widely in emergency situations because the initiation of treatment and alternation of devices may become more time-saving and efficient.

In addition to the technologies described above, the power source 60 may also use other nanotechnology, such as but not limited to: lithium sulfur batteries (using carbon nanofibers encapsulating the sulfur in the cathode or using mesoporous carbon nanoparticles that embraces sulfur inside the nanopores of the cathodes), nanocomposite batteries (using cathodes made of a nanocomposite designed to increase the energy density of the Li-ion batteries), nanostructured lithium titanate battery having enhancing charge/discharge capability, fast charge/recharge batteries using silicon nanoparticles coating a titanium disilicide lattice, thermocells using nanotubes that generate electricity, electrical generator built with nanostructured material that can generate electrical power from the user's body motion such as walking, and ultracapacitor batteries using single atom thick grapheme graphene sheets, and any combinations of batteries and power sources thereof.

Besides incorporating nanotechnology batteries, the power source 60 may also utilize other readily available supplies of electricity. For example, the power source 60 may be a power cord and power plug that can be directly connected to a common alternating current electricity outlet. Alternatively, the power source 60 may be a regular battery or battery pack, either rechargeable or non-rechargeable. The battery may be a regular AAA zinc-carbon or alkaline battery, or any other type or size that may fit the energy needs and/or physical accommodations of the current treatment device.

The heat source 10 is used to produce heat from the electricity generated by the power source 60. The design of the heat source 10 is generally known in the art and it may vary according to the characteristics of the electricity produced by the power source 60 and the specific requirements of the user and the injury/wound/infection to be treated. The heat source 10 may be a separate structure from the power source 60, or on the alternative, a part of an integrated structure, such as a heat generating body 70, which also includes the power source 60. The connection between the heat source 10 and the power source 60 may vary as well. In an alternative embodiment, the heat source 10 is removably attached to the power source 60, wherein after the heat source is considered to have produced enough heat, the power source 60 is detached from the heat source 10 and the rest of the treatment device 1, which is used to treat the wound bed or injury site, reducing the weight the treatment device and allowing the user of the treatment device to move around more freely. In another embodiment, the power source 60 may be connected to a plurality of heat sources 20 by long wires to ensure continued power supply to a number of treatment devices.

The heat applicator 20 is designed to apply the heat produced by the heat source 10 to the user of the treatment device. The heat applicator 20 in the current embodiment has a heat application layer 50 and a heat conductive layer 30. However, it should be noted that the heat application layer 50 and the heat conductive layer 30 may be a single layer integrated together and having both heat application and heat conducting capabilities. As to the embodiment shown in FIG. 2, the heat conductive layer may be made from woven or unwoven nanofibers that are extensively affixed to the back side of the heat application layer 50. The nanofibers used in the heat conductive layer 30 may include but not limited to: non-organic nanofibers such as ceramic nanofibers made from titanium dioxide ($TiO_2$), silicon dioxide ($SiO_2$), zirconium dioxide ($ZrO_2$), aluminum oxide ($Al_2O_3$), lithium titanate ($Li_4Ti_5O_{12}$), and titanium nitride (TiN) or platinum (Pt), organic or polymer nanofibers such as but not limited to polystyrene, polyacrylonitrile, polycarbonate, PEO, PET and water-soluble polymer nanofibers, and bi-component nanofibers, and any combinations thereof. The key property of the nanofibers making up the heat conductive layer 30 is that the nanofibers are capable of efficient transferring and distribution of heat. For example, the thermally treated carbon nanofibers produced by Aldrich (Pro. No. 719781) may be used for the heat conductive layer. In addition, the nanofibers of the heat conductive layer 30 may be capable of prolonged and controlled distribution of heat.

The heat application layer 50 is preferably made from thin and absorbent material so that it may evenly distribute the heat generated by the heat source to the wound bed or injury site and it may absorb the exudates, if any is produced by the wound or injury. As indicated above, the heat application layer 50 may be integrated with the heat conductive layer 30, forming a single layer. Thus, the materials usable for the heat conductive layer 30, as indicated above, may also be utilized for the heat application layer 50. In addition, the heat application layer 50 may be made from materials such as but not limited to: woven or unwoven fabric, cloth, terrycloth, woven or woven fibers of wool, flax, cotton, and/or yarn, mineral textiles such as but not limited to asbestos, glass and/or fiberglass, and synthetic textile including but not limited to nylon, polyester, and/or acrylic, or any combinations thereof. The heat application layer 50 may have a heat application surface 40, which may be sticky or have a sticky edge 45 to ensure covering or partial covering of the wound, infection or injury. The treatment device 1, in its unused form, may further include a non-sticky layer 75 attached to the heat application surface 40. The non-sticky layer 75 may be removed before use, allowing the treatment device to be securely attached.

In the current embodiment as shown in FIGS. 1, 2 and 3, the heat applicator 20 and heat generating body 70 are both shown as having a rectangular shape. It should be noted that the shape and size of the heat applicator 20 and the heat generating body 70, as well as various components of the treatment device 1, may vary according to the specific design of the device, the need of the user and the wound/infection/injury to be treated. The device and its components may take any shape also due to the extensive use of the current invention. For instance, the device may integrated into a mask, used for the treatment of acne with the capacity to activate specific regions conforming the area(s) of concern. As indicated below, the device herein disclosed may also utilize in applications that generally require thermal control. For example, the device may be made into pads, strips, or even clothing, in order to satisfy the specific need of the application. The size of the applicator may range from 1 $mm^2$ to 10 $m^2$, with the preferred range of 10 $mm^2$ to 100 $cm^2$. The weight of the treatment device 1 is preferable light, ranging from 0.1 g to 10 kg, and a preferred range of 1 g to 1 kg. The components of the device are preferably removably attached so that each part may be detached from the others and used separately. The applicator portion of the device may be cut or divided into intended size and shape to ensure convenient application.

Instead of a heat source 10, as indicated above, the treatment device 1 may include a refrigerating unit to make the treatment device capable of reducing temperature. Such an alternation allows the treatment device to be used similar as a cold pack, which may stabilize some injuries/wounds and facilitate recovery.

The current treatment device may be used for any kind of wounds, infections, injuries, and ailments. In addition, the current device may also be used to prevent wound infection by heating a target area prior to surgery. The basic function of the treatment device is to alter the temperature of an external injury site or wound bed to enhance healing and facilitate recovery. In addition, the current treatment device may be used for pain management, mainly by promoting blood flow and improving recovery. The current device may also be used to apply heat treatment for acne and other skin disorders, mainly by inhibiting the growth and development of bacteria affecting the illness. In organ transplantation, this device may be used to control and maintain the temperature of the transplant organs during transportation and storage of the transplant organs, as the organs require specific temperature control.

Beside its medical applications, the current device may also be used as other heating or cooling apparatus, such as but not limited to clothing apparel and accessories including gloves/hand warmers, jackets, pants, socks, shoe insert, ear muffs, footwear such as ski boots, and winter boots, ski equipment, goggles, ice skates, seat pads, portable seat cushions, and heatable or coolable containers. In particular, the device may be incorporated into mattress, bed cushions, mattress covers, comforters, pillows, and bed linens, etc., for the treatment of bed bugs, as bed bugs are sensitive to increased temperature. A thermal cover could also be used to encase an entire mattress and or bed. Alternatively, the current nanotech heating device may be included in a thermal bag, which may be used in the management of bed bugs by treating bed linens, comforters, pillows, as well as clothes. In addition, the fast-charging and long-lasting nature of the current device allows the device to be included a thermal blanket. The thermal blanket may be used for the treatment of hypothermia and the treatment of cardiac arrest with medically induced hypothermia. As long as the apparatus requires thermal control capability, the current invention may play a central role.

As indicated above, the treatment device may further comprise a control mechanism connected to the power source. The control mechanism may be used to initiate, terminate, and adjust the electricity provided by the power source, thus controlling thermal alternation capability of the device. With the control mechanism, the user of the treatment device may easily control the treatment process and change the durations, cycles, and intensity of the treatments.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A wound healing device, comprising:
   a heat source configured to increase vasodilation in a wound of a patient;
   a heat applicator connected to the heat source, the heat applicator comprising:
      a heat application layer having an application surface and a heat receiving surface with the heat application layer being configured to be applied to a skin surface of a patient, and a heat conductive layer having a front side and a back side,
      wherein the heat conductive layer comprises nanofibers embedded in the heat receiving surface of the heat application layer,
      wherein the heat conductive layer completely covers the heat receiving surface of the heat application layer, and wherein the heat application layer has an adhesive material disposed on a portion of the application surface;
   a power source connected to the heat source, empowering the heat source, the power source comprising at least one nanotech battery; and
   wherein the power source and the heat source are integrated into a heat generating body integral with the heat applicator,
      wherein the heat generating body has an area that is smaller than an area of the heat applicator.

2. The wound healing device of claim 1, wherein the heat applicator is a layered flat structure.

3. The wound healing device of claim 1, further comprising:
   a control mechanism connected to the power source, the control mechanism being capable of turning on, turning off, and adjusting an output of the power source.

4. The wound healing device of claim 1 wherein the heat application layer comprises an absorbent material.

5. The wound healing device of claim 1 further comprising a removable non-adhesive layer configured to cover the adhesive material.

* * * * *